(12) United States Patent
Minor

(10) Patent No.: US 7,324,677 B2
(45) Date of Patent: Jan. 29, 2008

(54) FEATURE QUANTITATION METHODS AND SYSTEM

(75) Inventor: James M. Minor, Los Altos, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 730 days.

(21) Appl. No.: 10/685,135

(22) Filed: Oct. 14, 2003

(65) Prior Publication Data

US 2005/0078860 A1    Apr. 14, 2005

(51) Int. Cl.
*G06K 9/00* (2006.01)

(52) U.S. Cl. .................. 382/129; 382/128; 382/170; 435/6

(58) Field of Classification Search ............ 382/128, 382/129
See application file for complete search history.

(56) References Cited

U.S. PATENT DOCUMENTS

| | | | |
|---|---|---|---|
| 5,948,902 A | 9/1999 | Honkanen et al. | |
| 6,171,797 B1 | 1/2001 | Perbost | |
| 6,180,351 B1 | 1/2001 | Cattell | |
| 6,221,583 B1 | 4/2001 | Kayyem et al. | |
| 6,222,664 B1 | 4/2001 | Dorsel | |
| 6,232,072 B1 | 5/2001 | Fisher | |
| 6,242,266 B1 | 6/2001 | Schliefer et al. | |
| 6,245,517 B1 * | 6/2001 | Chen et al. ............. | 435/6 |
| 6,251,588 B1 | 6/2001 | Shannon et al. | |
| 6,251,685 B1 | 6/2001 | Dorsel et al. | |
| 6,320,196 B1 | 11/2001 | Dorsel et al. | |
| 6,323,043 B1 | 11/2001 | Caren et al. | |
| 6,355,921 B1 | 3/2002 | Staton et al. | |
| 6,371,370 B2 | 4/2002 | Sadler et al. | |
| 6,406,849 B1 | 6/2002 | Dorsel et al. | |
| 6,486,547 B2 | 11/2002 | Dorsel et al. | |
| 6,518,556 B2 | 2/2003 | Staton et al. | |
| 6,591,196 B1 | 7/2003 | Yakhini et al. | |
| 6,674,882 B1 | 1/2004 | Shams | |
| 6,731,781 B1 * | 5/2004 | Shams et al. ............. | 382/129 |
| 2003/0215807 A1 | 11/2003 | Wolber et al. | |
| 2003/0216870 A1 | 11/2003 | Wolber et al. | |

FOREIGN PATENT DOCUMENTS

| WO | WO 01/81542 | 11/2001 |
|---|---|---|
| WO | WO 01/081542 | 11/2001 |

OTHER PUBLICATIONS

Search Report for British Patent Application No. 0422642.9, mailed Dec. 24, 2004, for counterpart of U.S. Appl. No. 10/685,135.
Tseng et al., "Issues in cDNA Microarray Analysis, Quality Filtering, Channel Normalization, Models of Variations and Assessment of Gene Effects". Nucleic Acids Research, 2001, vol. 29, No. 12, pp. 2549-2557.

(Continued)

*Primary Examiner*—Jingge Wu
*Assistant Examiner*—Sean Motsinger

(57) ABSTRACT

Methods, systems and recordable media for accurately reading and identifying high quality signals from a microarray feature. Signals may be identified and used regardless of their geographic/geometric locations and patterns within the feature zone. High quality signals may be read, identified and outputted from a microarray feature in a geometrically independent manner, such that the best quality signals are identified and useable, regardless of the locations or patterns in the region from which the best quality signals are outputted.

24 Claims, 11 Drawing Sheets

OTHER PUBLICATIONS

Press et al., *Numerical Recipes In C: The Art of Scientific Computing*; Cambridge University Press, 1988, pp. 248-250 and 558-565.

Haykin, Simon, *Adaptive Filter Theory*, Second Edition, 1991, Prentice Hall, Englewood Cliffs, NJ, pp. vi-ix.

Huber, Peter J., *Robust Statistics*, 1981, pp. v-viii, John Wiley & Sons, New York, NY.

Johnson et al., *Continuous Univariate Distribuitions*, vol. 1, Second Edition, 1994, Table of Contents, John Wiley & Sons, New York, NY.

efunda, "Radius Of Gyration Definition", downloaded Sep. 30, 2003, http://www.efunda.com/math/areas/RadiusOfGyrationDef.cfm.

Peraire, J., "Lecture D11-2D Rigid Body Kinetics: Equations of Motion", Unified Engineering, Spring 2003, Version 1.0, pp. 1-8.

\* cited by examiner

FEATURE QUANTITATION METHODS AND SYSTEM

FIELD OF THE INVENTION

The present invention relates to the processing of microarray data.

BACKGROUND OF THE INVENTION

Pharmaceutical, biotechnology, or genomics companies use polynucleotide arrays (such as DNA or RNA arrays), for example, as diagnostic or screening tools. Such arrays or microarrays include designed, localized regions (sometimes referenced as spots or features) each of a specific sequence of polynucleotides arranged in a predetermined configuration on a substrate such as a microchip. The arrays, when exposed to a sample, will exhibit a binding pattern. This binding pattern can be observed, for example, by labeling all polynucleotide targets (for example, DNA) in the sample with a suitable label (such as a fluorescent compound, radioisotope, molecular diode, or other know label), and accurately measuring all such labeled signals expressed on the array. Assuming that the different sequence polynucleotides were correctly deposited in accordance with the predetermined configuration, then the observed binding pattern will be indicative of the presence and/or concentration of one or more polynucleotide components of the sample. Such arrays geometrically (i.e., spatially) separate different gene expressions.

Biopolymer arrays can be fabricated using either in situ synthesis methods or deposition of the previously obtained biopolymers. "In situ" synthesis requires writing each component of the sequence at each probe location until the complete sequences are achieved according to a set of commands/instructions (scripts) that specify the desired sequences. I situ synthesis may be carried out by a number of different processes, including, but not limited to, phosphoamidite processes or photolithographic methods, for example. The deposition methods basically involve depositing biopolymers at predetermined locations on a substrate which are suitably activated such that the biopolymers can link thereto. Biopolymers of different sequence may be deposited at different regions of the substrate to yield the completed array. Washing or other additional steps may also be used. Procedures known in the art for deposition or writing of polynucleotides, particularly DNA such as whole oligomers or cDNA, include touching drop dispensers to a substrate or use of an ink jet type head to fire drops onto the substrate.

Each deposition or in situ layer, performed by any of the techniques, is deposited to within a designated localized area, e.g., the feature zone or area of which is predetermined and generally having a polygonal shape (rectangular, square, hexagonal, octagonal or the like) of predetermined dimensions designed to closely pack the probe features on the array to maximize the number of gene probes that can be efficiently included on the array, and still effectively read from the array.

Labeled biological sample(s) (i.e., "target") are then prepared, labeled and hybridized to the probes on the array, although other method of detection without labels have previously been described and may be alternatively processed.

Typically, radioactivity or some form of electromagnetic energy is used to measure responses at each probe. For example, a scanner may be used to read the fluorescence of these resultant surface bound molecules under illumination with suitable (most often laser) light. The scanner acts like a large field fluorescence microscope in which the fluorescent pattern caused by binding of labeled molecules is scanned on the chip. In particular, a laser induced fluorescence scanner provides for analyzing large numbers of different target molecules of interest, e.g., genes/mutations/alleles, in a biological sample.

The scanning equipment typically used for the evaluation of microarrays includes a scanning fluorometer. A number of different types of such devices are commercially available from different sources, such as Axon Instruments in Union City, Calif.; Perkin Elmer of Wellesly, Mass.; and Agilent Technologies, Inc. of Palo Alto, Calif. Analysis of the data, (i.e., collection, reconstruction of image, comparison and interpretation of data) is performed with associated computer systems and commercially available software, such as GenePix by Axon Instruments, QuantArray by Perkin Elmer, Feature Extraction by Agilent of Palo Alto, Calif., or Affy Scanner, available from Affymetrix, Santa Clara, Calif.

In such scanning devices, an array, or portion thereof, is simultaneously scanned and imaged, such as with the use of a CCD sensor, for example and electronically read to interpret signal intensities of the scan. Such intensities, as a function of position, are typically referred to in the art as "pixels" or "pixel values." Collectively, the pixels make up a microarray scan image having a multiplicity of feature cells, wherein each probe feature cell is comprised of a group of pixels. Commonly used feature sizes include features which are each made up various resolution, e.g., 100 pixels (10×10 pixel spot size) or features each made up of 400 pixels (20×20 pixel spot size), for example, although such sizes may vary and are predetermined before manufacture of the array. Each pixel over a probe location contains the signals from many millions of sequences at the probe at least. Some of the sequences are distorted from their scripted design by noise factors. Some sequences are attached to labeled sequences from the target that are particularly noisy. However, there is generally a subpopulation of probe sequences that produce superior signal strength and low noise. Different pixels capture more or less of this subpopulation of high quality signals. The present invention directly and efficiently identifies the set of pixels that best capture the high-quality subpopulation for each probe/feature on a microarray.

On two color (two channel) systems, direct comparisons are optimal between two different biological samples, wherein one sample is encoded with a green fluorescing dye and the other is encoded with a red fluorescing dye, for example. The differential gene expression between the two samples is then given by the color at each probe because the color is determined by how much red fluorescence and green fluorescence is present at each probe. With a one color, or single channel system, absolute signals or intensities are measured. With a single channel system, one biological sample may be measured on a microarray, and a second biological sample can be measured on a second microarray. The readings are then compared to determine ratios between the results of the two arrays.

The scanner output may be represented as an image file of ordered sequential signals (such as a TIFF file, for example). Image processing is then performed to organize signal patterns and quantitate the value at each feature (localized probe or "spot"), or to evaluate the values of red and green at each feature for a two channel system. Once the features values are determined, ratios can be calculated.

In array fabrication, the quantities of biochemicals or DNA available for the array are usually very small and expensive. Sample quantities available for testing are usually also very small and it is therefore desirable to simultaneously test the same sample against a large number of different probes on an array. These conditions require use of arrays with large numbers of very small, closely spaced spots.

The use of microarray technologies to conduct experiments that measure thousands of genes and proteins simultaneously and under different conditions are becoming the norm in both academia and pharmaceutical/biotech companies. Microarray technology is leading to greater feature density as well as to extremely high-resolution scanning. In their largest capacities, such as in a full human genome catalog array, there may be as many as three or four 25,000 to 100,000-feature cells. This results in increasingly large amounts of both image and feature analysis data which can be problematic for several reasons. First the higher the density of features on an array, the increasingly more difficult it becomes to accurately extract these features. Higher accuracy and precision of the scanning apparatus becomes necessary. Even more importantly, higher accuracy and precision of the manufacturing techniques, preparation techniques, and associated apparatus are required, so that at the user end, the user can located the information to be read and distinguish it from noise.

Currently, arrays from different sources and/or manufacturers vary greatly in quality. Variations in both signal and optical properties of probes on an array occur due to poor stability/quality or errors in the application of the features to the chip. Ideally, when the features are dots or spots, each should be well-formed (e.g., a substantially perfect circle) and uniformly spaced. As hybridized, typically a rim is formed around a slightly indentured center producing a halo effect. With the wide variation of manufacturers now available, however, the feature images are not always so homogeneous. For example, fluorescent "doughnuts" (i.e., a dot only filled circumferentially along the perimeter, with at least a partial blank or hole, or even a spike in the center) may be formed in some instances, rather than a fully filled circle with only slight indenture. Other partially formed or mis-formed features or manufacturing may also occur, such as crescent-shaped features; "measled" spot images, irregular boundaries (perimeters) of the features; misaligned rows or columns of features; misalignment between consecutive features, along a row and/or a column; variations in the size or circumferences of the dots; and others.

Most quantitation methods are based on the intended design of the feature spatial pattern for an array as printed or written. That is, most quantitation methods "look for" the configuration of the signal spot (i.e., feature) as it was intended to look by its predetermined geometry and dimensions. This technique is often referred to in the art as using a "cookie cutter" to outline the feature with a template or "cookie cutter" of the predetermined shape and size, which is positioned within each area of the microarray that is laid out to have a feature deposited or written thereon, in a location where it is determined that the best defined feature is represented. For example, when an array is divided into squares of predetermined equal geometries within each of which it is intended to deposit or write a circular spot or feature (with each feature intended to have the same diameter and be clearly geometrically separated from all adjacent features), the cookie cutter is used to define a circle that captures adjacent pixels having a predetermined minimum radius, within each square area of pixels, that outputs the highest quality ensemble signal. External pixels (outliers) are removed from consideration. This technique becomes problematic with occurrences of malformed features, examples of which were mentioned above.

When malformed features are present (which are quite common occurrences) the cookie cutter methods may not find a generally uniform signal that is shaped in the predetermined shape of the feature, and may have difficulty determining where to locate the best placement for the location of the feature. Further, even if the cookie cutter is successful in determining where to locate each feature, such locations tend to be more non-specific due to the introduction of noise and randomness by the malformed features.

What is needed are better techniques for identifying and using the signals from those sequences on a microarray that are of good quality, that most closely (maybe perfectly) match the sequence that was intended to be deposited. Further, improved techniques for identification and selection of the highest quality signals without the use of localized-based geometric patterns, such as cookie-cutters is needed, to better account for malformed features which may include high quality signals in what would otherwise be considered "outlier pixels" by a cookie cutter method and thus discarded.

SUMMARY OF THE INVENTION

The present invention provides methods, systems and recordable media for accurately reading and identifying high quality signals from a microarray feature. Such signals may be identified and used regardless of their geographic locations within the feature.

By providing a bounded-localized region of an array that contains a feature, wherein the region is broken down into subunits that cover an entire surface of the region and only a portion of the subunits cover an area on which the feature exists, all subunits are read to obtain an output signal for each subunit. The output signals from the subunits read are rank ordered according to signal magnitude. From such a rank ordering, a subset of the rank ordered output signals may be identified, which contain the highest quality signals of the feature.

The coordinates of the locations of the subunits on the region are maintained in association with the output signal values even after rank ordering, so that the subunits providing the high quality signals can be geographically/geometrically located on the region.

The output signal magnitudes may be plotted versus rank order numbers on a two-dimensional plot.

In addition to identifying a subset containing the highest quality signals (e.g., "halo signals") any and all of the following subsets may be identified from the read signals: a residue subset comprising a subset of the rank ordered output signals having magnitudes larger than the high quality signals subset; a background subset comprising a subset of the rank ordered output signals having the lowest magnitudes; a corona subset comprising a subset of the rank ordered output signals having transitional magnitude values between the values of the background subset and the subset having the high quality signals; and a semi-background subset, having higher values than the background section, but lower than the transitional values of the corona subset.

By comparing the output signal values with the coordinate locations of the subunits, banding patterns may be identified, and diagnostics may be produced based on the banding patterns. Diagnostics may be produced with regard to one or more of the identified subsets. Diagnostics that may be produced include, but are not limited to: estimating a radius; computing a radius of gyration; calculating a mean, median or other average estimate of signal values; calculating a standard deviation of signal values; calculating a signal range; calculating a signal differential value among subsets; calculating shift metrics; zero-balancing signal values; depurination-slope of halo signals; and other diagnostics that would be readily apparent to those of ordinary skill in the statistical arts.

Two corona section locations may be identified to be used for comparison with two corona sections identified in other channels of a multi-channel array, to check scanner alignment among the multiple channels.

For example, for a two-color platform, by comparing output signals of a first channel with those of a second channel in the two-channel (color) system, misalignment of the channels may be identified and corrected.

Comparisons of output signals between channels may be performed on the basis of rank order of the output signal values, not physical location of corresponding subunit on the region, to give better expression ratios. Hence, exact scanner alignment is not necessary.

The present invention provides methods, systems and recordable media for selecting high quality signals from a microarray feature in a geometrically independent manner, such that the best quality signals are identified and useable, regardless of the locations in the region from which the best quality signals are outputted.

By providing an array divided into a grid of regions estimated to each contain a feature, wherein each said region is broken down into subunits that cover an entire surface of the region and only a portion of the subunits cover an area on which the feature may exist, all subunits are read to obtain an output signal for each subunit. The output signal results are rank ordered according to signal magnitude, and this rank ordering is processed to identify a subset containing the best quality signals. The process may be repeated for each region.

Further provided are means for locating a grid to define the regions to be analyzed for high quality signals.

Further covered are forwarding a result obtained from any of the methods discussed, transmitting data representing a result obtained from the any of the methods discussed, as well as receiving a result obtained from any of the methods discussed.

These and other advantages and features of the invention will become apparent to those persons skilled in the art upon reading the details of the invention as more fully described below.

DETAILED DESCRIPTION OF THE INVENTION

Figure 1:
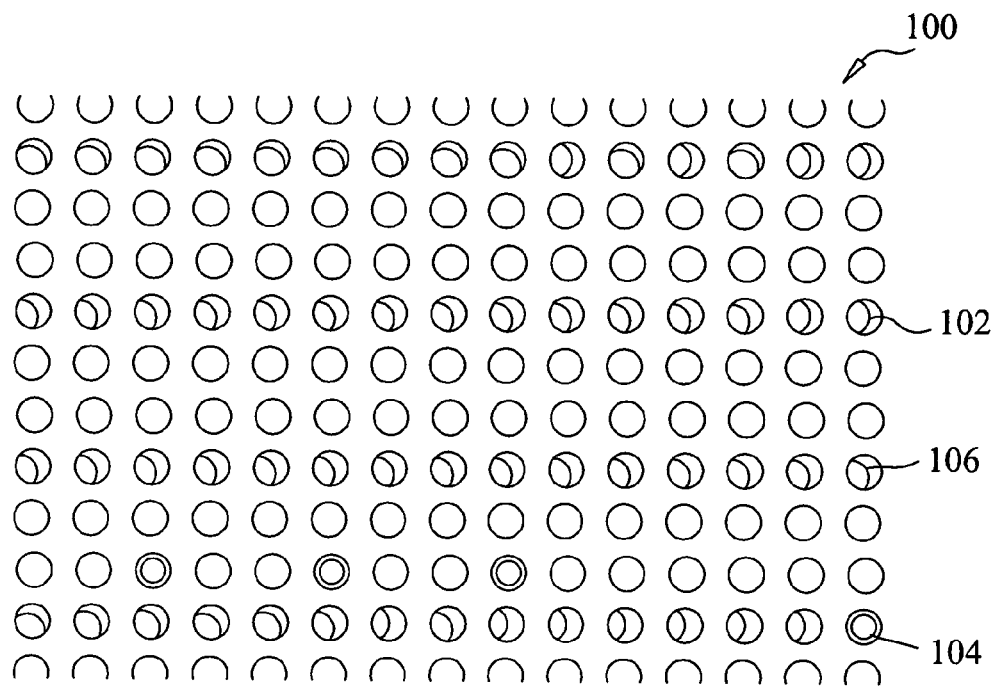
FIG. 1 shows an example of a portion of an electronic image of microarray results from labeling polynucleotide targets.

Before the present system and methods are described, it is to be understood that this invention is not limited to particular arrays, hardware or software described, as such may, of course, vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "a feature" includes a plurality of such features and reference to "the array" includes reference to one or more arrays and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DEFINITIONS

In the present application, unless a contrary intention appears, the following terms refer to the indicated characteristics.

A "biopolymer" is a polymer of one or more types of repeating units. Biopolymers are typically found in biological systems and particularly include polysaccharides (such as carbohydrates), and peptides (which term is used to include polypeptides and proteins) and polynucleotides as well as their analogs such as those compounds composed of or containing amino acid analogs or non-amino acid groups, or nucleotide analogs or non-nucleotide groups. This includes polynucleotides in which the conventional backbone has been replaced with a non-naturally occurring or synthetic backbone, and nucleic acids (or synthetic or naturally occurring analogs) in which one or more of the conventional bases has been replaced with a group (natural or synthetic) capable of participating in Watson-Crick type hydrogen bonding interactions. Polynucleotides include single or multiple stranded configurations, where one or more of the strands may or may not be completely aligned with another.

A "nucleotide" refers to a sub-unit of a nucleic acid and has a phosphate group, a 5 carbon sugar and a nitrogen containing base, as well as functional analogs (whether synthetic or naturally occurring) of such sub-units which in the polymer form (as a polynucleotide) can hybridize with naturally occurring polynucleotides in a sequence specific manner analogous to that of two naturally occurring polynucleotides. For example, a "biopolymer" includes DNA (including cDNA), RNA, oligonucleotides, and PNA and other polynucleotides as described in U.S. Pat. No. 5,948, 902 and references cited therein (all of which are incorporated herein by reference), regardless of the source.

An "oligonucleotide" generally refers to a nucleotide multimer of about 10 to 100 nucleotides in length, while a "polynucleotide" includes a nucleotide multimer having any number of nucleotides. A "biomonomer" references a single unit, which can be linked with the same or other biomonomers to form a biopolymer (for example, a single amino acid or nucleotide with two linking groups one or both of which may have removable protecting groups). A biomonomer fluid or biopolymer fluid reference a liquid containing either a biomonomer or biopolymer, respectively (typically in solution).

A "mer" refers to a link, such as a nucleic acid, nucleotide or residue, in a sequence of such nucleic acids, nucleotides or residues.

An "array", "microarray" or "bioarray", unless a contrary intention appears, includes any one-, two- or three-dimensional arrangement of addressable regions bearing a particular chemical moiety or moieties (for example, biopolymers such as polynucleotide sequences) associated with that region. An array is "addressable" in that it has multiple regions of different moieties (for example, different polynucleotide sequences) such that a region (a "feature" or "spot" of the array) at a particular predetermined location (an "address") on the array will detect a particular target or class of targets (although a feature may incidentally detect non-targets of that feature). Array features are typically, but need not be, separated by intervening spaces. In the case of an array, the "target" will be referenced as a moiety in a mobile phase (typically fluid), to be detected by probes ("target probes") which are bound to the substrate at the various regions. However, either of the "target" or "target probes" may be the one which is to be evaluated by the other (thus, either one could be an unknown mixture of polynucleotides to be evaluated by binding with the other).

An "array layout" refers to one or more characteristics of the features, such as feature positioning on the substrate, one or more feature dimensions, and an indication of a moiety at a given location. "Hybridizing" and "binding", with respect to polynucleotides, are used interchangeably. A "pulse jet" is a device which can dispense drops in the formation of an array. Pulse jets operate by delivering a pulse of pressure to liquid adjacent an outlet or orifice such that a drop will be dispensed therefrom (for example, by a piezoelectric or thermoelectric element positioned in a same chamber as the orifice).

When one item is indicated as being "remote" from another, this is referenced that the two items are at least in different buildings, and may be at least one mile, ten miles, or at least one hundred miles apart.

"Communicating" information references transmitting the data representing that information as electrical signals over a suitable communication channel (for example, a private or public network).

"Forwarding" an item refers to any means of getting that item from one location to the next, whether by physically transporting that item or otherwise (where that is possible) and includes, at least in the case of data, physically transporting a medium carrying the data or communicating the data.

A "region" refers to any finite small area on the array that can be illuminated and any resulting fluorescence therefrom simultaneously (or shortly thereafter) detected, for example a pixel.

"Banding" refers to grouping patterns of coordinates associated with output signals that may occur when the output signals have been rank-ordered according to relative intensity levels.

A "processor" references any hardware and/or software combination which will perform the functions required of it. For example, any processor herein may be a programmable digital microprocessor such as available in the form of a mainframe, server, or personal computer (desktop or portable). Where the processor is programmable, suitable programming can be communicated from a remote location to the processor, or previously saved in a computer program product (such as a portable or fixed computer readable storage medium, whether magnetic, optical or solid state device based). For example, a magnetic or optical disk may carry the programming, and can be read by a suitable disk reader communicating with each processor at its corresponding station. Reference to a singular item, includes the possibility that there are plural of the same items present.

"May" means optionally.

Methods recited herein may be carried out in any order of the recited events which is logically possible, as well as the recited order of events.

All patents and other references cited in this application, are incorporated into this application by reference except insofar as they may conflict with those of the present application (in which case the present application prevails).

Reference to a singular item, includes the possibility that there are plural of the same items present.

"May" means optionally.

Methods recited herein may be carried out in any order of the recited events which is logically possible, as well as the recited order of events.

A "subarray" or "subgrid" is a subset of an array. Typically, a number of subgrids are laid out on a single slide and are separated by a greater spacing than the spacing that separates features or spots or dots.

"Residue" refers to an error-prone or non-specific sequence or group of sequences within a feature which have non-specific binding properties and generally produce a high or "spiked" output signal when processed, due to the non-specific nature of the moieties that bind to the residue.

Any given substrate may carry one, two, four or more arrays or subarrays disposed on a front surface of the substrate. Depending upon the use, any or all of the arrays/subarrays may be the same or different from one another and each may contain multiple spots or features. A typical array may contain more than ten, more than one hundred, more than one thousand more ten thousand features, or even more than one hundred thousand features, in an area of less than 20 cm$^2$ or even less than 10 cm$^2$. For example, features may have widths (that is, diameter, for a round spot) in the range from a 10 µm to 1.0 cm. In other embodiments each feature may have a width in the range of 1.0 µm to 1.0 mm, usually 5.0 µm to 500 µm, and more usually 10 µm to 200 µm. Non-round features may have area ranges equivalent to that of circular features with the foregoing width (diameter) ranges. At least some, or all, of the features are of different compositions (for example, when any repeats of each feature composition are excluded the remaining features may account for at least 5%, 10%, or 20% of the total number of features), each feature typically being of a homogeneous composition within the feature. Interfeature areas (e.g., background) will typically (but not essentially) be present which do not carry any polynucleotide (or other biopolymer or chemical moiety of a type of which the features are composed). Such interfeature areas/background typically will be present where the arrays are formed by processes involving drop deposition of reagents but may not be present when, for example, photolithographic array fabrication processes are used. It will be appreciated though, that the interfeature areas, when present, could be of various sizes and configurations.

Each array may cover an area of less than 100 $cm^2$, or even less than 50 $cm^2$, 10 $cm^2$ or 1 $cm^2$. In many embodiments, the substrate carrying the one or more arrays will be shaped generally as a rectangular solid (although other shapes are possible), having a length of more than 4 mm and less than 1 m, usually more than 4 mm and less than 600 mm, more usually less than 400 mm; a width of more than 4 mm and less than 1 m, usually less than 500 mm and more usually less than 400 mm; and a thickness of more than 0.01 mm and less than 5.0 mm, usually more than 0.1 mm and less than 2 mm and more usually more than 0.2 and less than 1 mm. With arrays that are read by detecting fluorescence, the substrate may be of a material that emits low fluorescence upon illumination with the excitation light. Additionally in this situation, the substrate may be relatively transparent to reduce the absorption of the incident illuminating laser light and subsequent heating if the focused laser beam travels too slowly over a region. For example, substrate 10 may transmit at least 20%, or 50% (or even at least 70%, 90%, or 95%), of the illuminating light incident on the front as may be measured across the entire integrated spectrum of such illuminating light or alternatively at 532 nm or 633 nm.

Arrays can be fabricated using drop deposition from pulse jets of either polynucleotide precursor units (such as monomers) in the case of in situ fabrication, or the previously obtained polynucleotide. Such methods are described in detail in, for example, the previously cited references including U.S. Pat. Nos. 6,242,266, 6,232,072, 6,180,351, 6,171,797, 6,323,043, U.S. patent application Ser. No. 09/302,898 filed Apr. 30, 1999 by Caren et al., and the references cited therein. As already mentioned, these references are incorporated herein by reference. Other drop deposition methods can be used for fabrication, as previously described herein. Also, instead of drop deposition methods, photolithographic array fabrication methods may be used. Interfeature areas need not be present particularly when the arrays are made by photolithographic methods as described in those patents. Further, "in-situ" synthesis methods may be employed for fabricating biopolymer arrays, as already described above.

Following receipt by a user of an array made by any of the techniques described above, it will typically be exposed to a sample (for example, a fluorescently labeled polynucleotide or protein containing sample) and the array then read. Reading of the array may be accomplished by illuminating the array and reading the location and intensity of resulting fluorescence at multiple regions on each feature of the array. For example, a scanner may be used for this purpose which is similar to the AGILENT MICROARRAY SCANNER manufactured by Agilent Technologies, Palo Alto, Calif. Other suitable apparatus and methods are described in U.S. patent application Ser. No. 10/087,447 "Reading Dry Chemical Arrays Through The Substrate" by Corson et al.; and in U.S. Pat. Nos. 6,518,556; 6,486,457; 6,406,849; 6,371,370; 6,355,921; 6,320,196; 6,251,685; and 6,222,664. However, arrays may be read by any other method or apparatus than the foregoing, with other reading methods including other optical techniques (for example, detecting chemiluminescent or electroluminescent labels) or electrical techniques (where each feature is provided with an electrode to detect hybridization at that feature in a manner disclosed in U.S. Pat. Nos. 6,251,685, 6,221,583 and elsewhere). A result obtained from the reading followed by a method of the present invention may be used in that form or may be further processed to generate a result such as that obtained by forming conclusions based on the pattern read from the array (such as whether or not a particular target sequence may have been present in the sample, or whether or not a pattern indicates a particular condition of an organism from which the sample came). A result of the reading (whether further processed or not) may be forwarded (such as by communication) to a remote location if desired, and received there for further use (such as further processing).

The present invention relates to processing of microarray data. More particularly, the present invention is directed to systems and methods for microarray quantitation and quality control for locating and using the high quality signals provided within defined areas that bound every microarray probe or feature. The defined regions may be completely general in size and shape and not restricted to be the same for all features. Referring now to FIG. 1, an example of a portion of a an electronic image 100 (.tif file) of microarray results from labeling polynucleotide targets (for example, DNA) in the sample with a suitable label (such as a fluorescent compound), and accurately observing the fluorescent signals on the array is shown. Even with the naked eye, it is readily observable that not all features are well formed and consistently fluorescent. For example, feature 102 shows increased intensity in the left side portion of the feature, compared to the rest of the feature/spot, and feature 104 shows a rim or perimeter having a different intensity than the central portion of the feature, appearing almost doughnut-shaped. Feature 106 appears crescent-shaped and would likely prove difficult to properly center with a "cookie-cutter" approach, since the center of intensity is not at the center of the feature 106. Although not shown in FIG. 1, many features in practice occur in even much less uniform condition than those discussed.

Rather than trying to locate the exact positions of the features of a microarray and then reading the signals from within those identified locations, such as done by the "cookie-cutter" methods referred to above, the present invention reads substantially all of the information from the pixels over the microarray to determine where the best signals are being generated. Thus, the present invention takes a "non-spot-based" approach to finding a subset of sequences within each feature that are ideal or close to ideal representation of the sequences that were intended to be deposited on the microarray for that particular feature.

Figure 2:
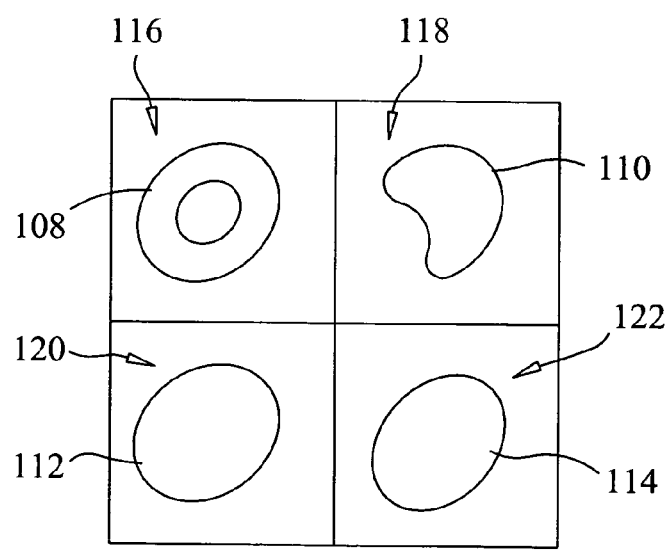
FIG. 2. is a schematic view of four features contained within equal sized regions from an array.

As can be seen in FIG. 1, each feature is separated by a consistent spacing, relative to an appropriate coordinate system such as x and y coordinates or hexagonal close-packed coordinates, for example, of a grid along which the features are deposited. According to the present invention, a region is defined and located for each feature, that encapsulates each feature and separates it out from the other features. In the example of FIG., 1, the regions could be defined a squares for example, which is illustrated with regard to just four features 108, 110, 112, 114 in FIG. 2. By considering the output of each pixel in each region 116, 118, 120 and 122 (which in the example of FIG. 2 are squares, although other shapes of repeating area may be defined), this ensures that all of the signals from the sequences forming the feature within that region are considered. Accordingly, the present invention employs simpler techniques for quantitating the values of the features than current methods, since there is no need to "hone in" or "target" the best location where a feature is thought to exist.

Figure 3A:
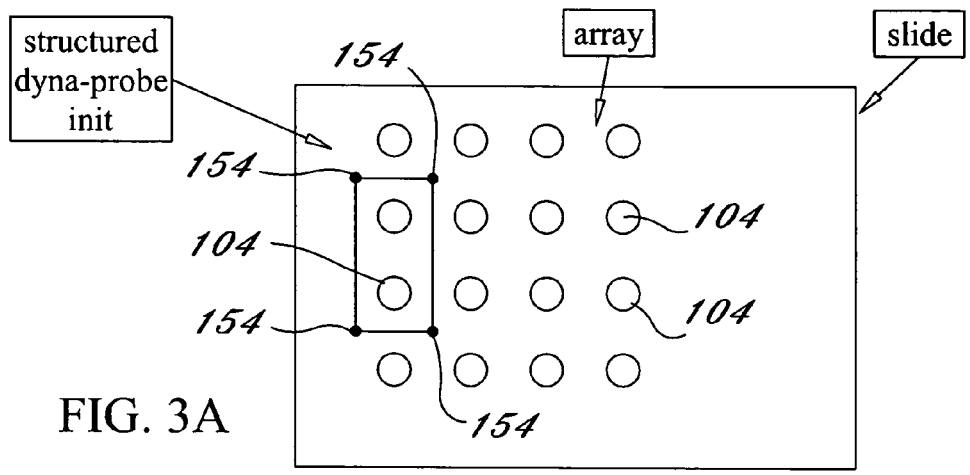
FIGS. 3A-3C schematically illustrate steps that may be employed for locating features on an array grid.

Rather, all pixels inside a region are considered (e.g., all pixels in square 120 are read to determine the best signal from feature 112). The regions are generally defined or determined by the array manufacturer's specifications as to the regions defined for depositing features thereon. However, it is still necessary to define a starting point, even when the dimensions of the regions are known, i.e., where does one region end and another begin? Various techniques may be employed for locating one or more features as a sampling to determine a starting location for identifying where each regions begins and ends. One such technique involves using dynamic data clustering techniques, as described in co-pending, commonly assigned application Ser. No. 09/986,746, filed Nov. 9, 2001 and titled "System and Method for Dynamic Data Clustering". application Ser. No. 09/986,746 is hereby incorporated herein, in its entirety, by reference thereto. Using such techniques, with the mathematical probe provided (not to be confused with the physical array probes or features), the mathematical probe may be implemented as a multiplicity of probes (e.g., see probes 154 in FIG. 3A) spaced apart according to the array grid design where features 104 are predesigned to be located. The structured, expanded (i.e., multiplicity of mathematical probes) mathematical probe 154 is used as described with reference to a single mathematical probe in application Ser. No. 09/986,746, but provides more leverage for this application, i.e., for a designed spread of spot clusters formed by the array features as optical/signal clusters.

Figure 3B:
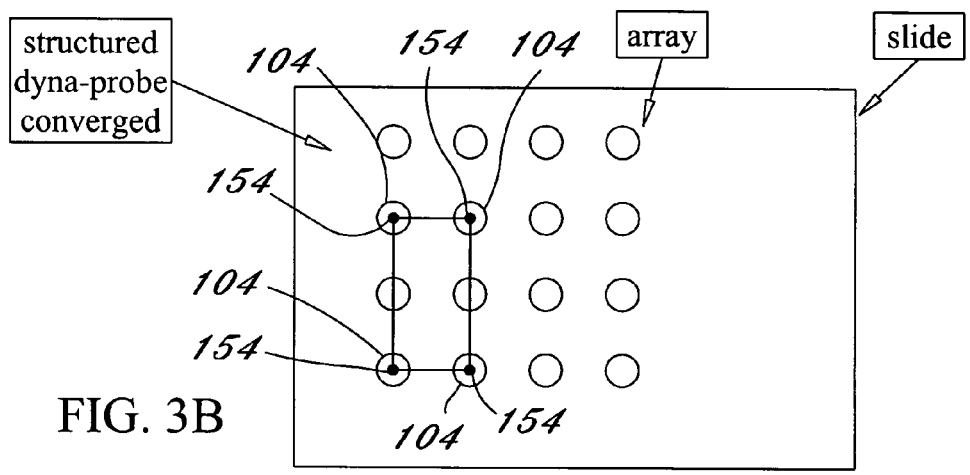
Figure 3C:
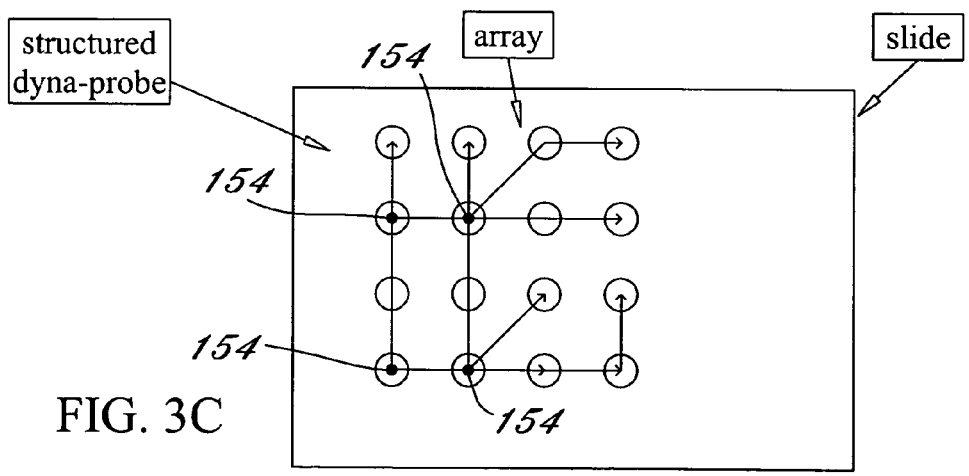

Once the DynaCluster™ (available from Agilent Technologies Inc. Palo Alto, Calif.) mathematical probes 154 converge on features 104 in an array (as shown schematically in FIG. 3B), the array locations of all features may be determined therefrom. Although this structured multiple mathematical probe approach may be applied to encompass all feature locations, it may be applied alternatively to a random or predetermined subset of features to locate such features, and then calculate the remaining feature locations from the results, as illustrated in FIG. 3C. The latter alternative may be more computationally economical, and require less processing time. The remaining feature locations (identified by the arrows pointing to them in FIG. 3C) may be calculated from the spacing of the probes 154 and any predetermined spacing/coordinate information provided by the manufacturer of the array.

Alternative techniques may be employed to locate the grid, so as to know where to establish the boundaries of the regions, including those described in co-pending, commonly assigned application Ser. No. 10/449,175, filed May 30, 2003 and titled "Feature Extraction System and Methods", for example. application Ser. No. 10/449,175 is hereby incorporated herein, in its entirety, by reference thereto. Using these techniques, the grid is automatically located based upon projecting the two dimensional array into two one-dimensional vectors and peak processing the vectors to determine locations of the features. Other techniques for locating and/or ordering features are provided in the following applications, each of which is incorporated herein, in its entirety, by reference thereto: application Ser. No. 10/140,575; application Ser. No. 10/153,345; application Ser. No. 10/143,547; and application Ser. No. 10/639,184.

Once the regions have been established, processing of each pixel within a region is performed to determine a signal level for each pixel within that region. Typically, RLU (relative luminosity units) are read from the features, based upon the amount that they fluoresce. However, signal levels that may be interpreted according to the present invention may also be in the form of radioactivity levels, or other forms of electromagnetic energy, as indicated above. Pixels and their properties (e.g., resolution, offset, etc.) are constructed by the scanner reading the array. The present invention is also capable of identifying misalignment between the two colors of a two-channel array, at the feature edges, by comparing the pixel-processed signals from the two colors for each feature. This is referred to as a "scanner shift metric". Since the present invention is very adept at locating the corona locations of features (as described in more detail below) the corona locations of the two colors may be compared to one another at the top and bottom edges or border of a feature, where scanners tend to be most sensitive or prone to misalignment. These locations should overlap (i.e., lie on top of one another), but when they do not, this indicates misalignment of the two channels. When misalignment is detected, a row-shift of one of the color zones of the scanner may be performed to better overlap the colors as read. Scanner shift metrics may be robustly created for all scanner alignment errors, for all channels. However, perfect scanner alignment is not required for two-color or multiple-channel (color) (e.g., nano-diode technology) systems, since the signal values are profiled according to rank order, and not by comparing the exact pixel locations with one another as done by conventional methods, as described herein.

All pixels are read and processed, including those that only represent background surrounding a feature and do not output a signal representative of sequences within the feature. Each pixel representative of the feature encapsulates a population of sequences, both bad and good, which the present invention processes and ranks to determine the best signal from a feature. Thus, the present invention does not assume any kind of geometry of the feature or spot.

By reading each pixel within a region and processing to pick out the pixels with the highest quality signals, the most reliable signal for a feature can be determined. The pixels having the highest quality signals imply that those pixels have a higher number of perfect sequences than the other pixels giving lesser quality signals, since the perfect sequences attract mostly only the intended moieties and thus give the most consistent, non-background signal levels. Target-label distributions impact signal quality as well. Hence, the best signal result from high-quality sequences combined to target sequences with minimal label impact on its hybridization efficiency. If a pixel represents a location of a feature that has a lot more good or perfect sequences than it has low quality sequences, then the signal read from that pixel will be relatively high. However, such good sequences (and hence "good pixels") can be located anywhere geometrically within the feature, in the middle, on the edge, etc. In instances where good pixels are located on an edge or perimeter, for example, a cookie-cutter could miss good signals completely by locating the cookie-cutter template which defines "the feature" to be interpreted, such that it slightly misses a perimeter (of a feature) that contains high quality signals. In contrast, the present invention does not miss good sequences that are bound/hybridized with the best members of the labeled-target population, regardless of where they are located within the region.

If a pixel being read according to the present techniques contains no sequences (i.e., it is located in the background of the region and not part of the feature) or has sequences with no systematic pattern, e.g., dominated by a lot of errors, it will have a relatively low signal (or an extremely high spike, if residue is contained in that location, since residue isn't selective as to moieties and attracts many different sequences of them). The present invention sorts out such low signals and abnormally high signals in determining the best signals outputted from a region.

Figure 4:
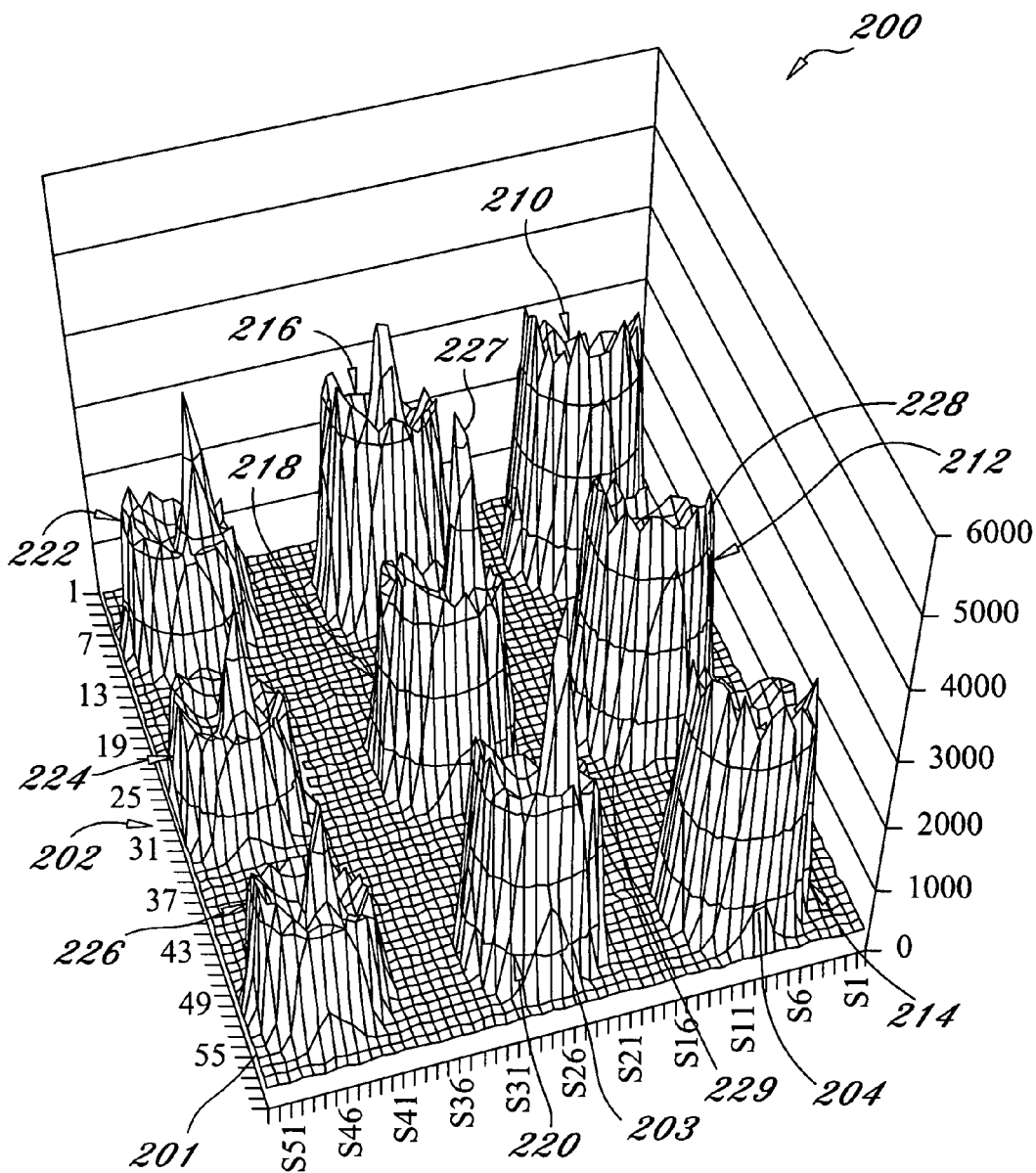
FIG. 4 is a three-dimensional plot of output signals from nine representative features from a portion of a microarray.

FIG. 4 is a three-dimensional plot 200 of signal outputs from nine representative features from a portion of a microarray. Notice that each small square 201 represents a single pixel, and that the pixels 201 (both active (i.e., outputting signals representative of features) and inactive) completely cover the grid 202 on which the features 210, 212, 214, 216, 218, 220, 222, 224 and 226 are located. The units of intensity may be RLU, or other typical scanner output units, for example. The scale that runs horizontally in FIG. 4 and which includes S51, S46, etc. refers to the pixel column numbers and the vertical scale on the left hand side of FIG. 5 refers to pixel row number.

Features 210, 212 and 214 are the highest quality signals in this example are sixty-mer features resultant from attracting matched twenty-five-mer targets that the sixty-mer features were built to match. Forty-five-mer features 216, 218 and 220 were built to attract twenty-five-mer targets and give the medium quality signals shown in FIG. 4. Twenty-five-mer features 222, 224 and 226 were built to bind with twenty-five-mer targets and give the lowest signals relative to the others shown in FIG. 4.

It can be observed that the background pixels output the lowest signals, e.g., see pixel 201, and these levels can be optionally used as a signal level to be subtracted out from the feature signal levels to zero out the background levels. At the edges of each feature is a region commonly referred to as the corona, where signal levels are in transition between the background level and signal levels that reliably represent the sequence meant to be measured on the feature, e.g., see pixels 203 and 204 which are in the corona region. Feature 212 was considered to give the highest quality signal overall in FIG. 4, as it can be seen that the signal values over the pixels just past the corona section give the most consistent values, relative to all other features in FIG. 4. Several features show spiked output values (e.g., see spikes 227 and 229) which are likely due to residues within those respective features, or a large concentration of erroneous sequences in those locations. The present invention inherently filters out such regions so that they are not used as a representation of a signal for a feature, thereby reducing noise and improving accuracy of the readings.

It can also be observed that the strongest or highest consistent signals in these features are often located on the perimeter or rim of the feature, such as at 228, for example. Again, it is noted that a cookie-cutter approach to reading such a configuration for a feature runs the risk of some mixing of the best portions having the best signals with portions having mediocre signals in a feature. Using the present techniques, all of the best signals are read and used in representation of a feature to provide the highest quality signal there from. The feature or spot does not have to be in the middle of a region; the feature or spot does not even have to appear as a spot. Adjacency of the best signals is not assumed.

Figure 5:
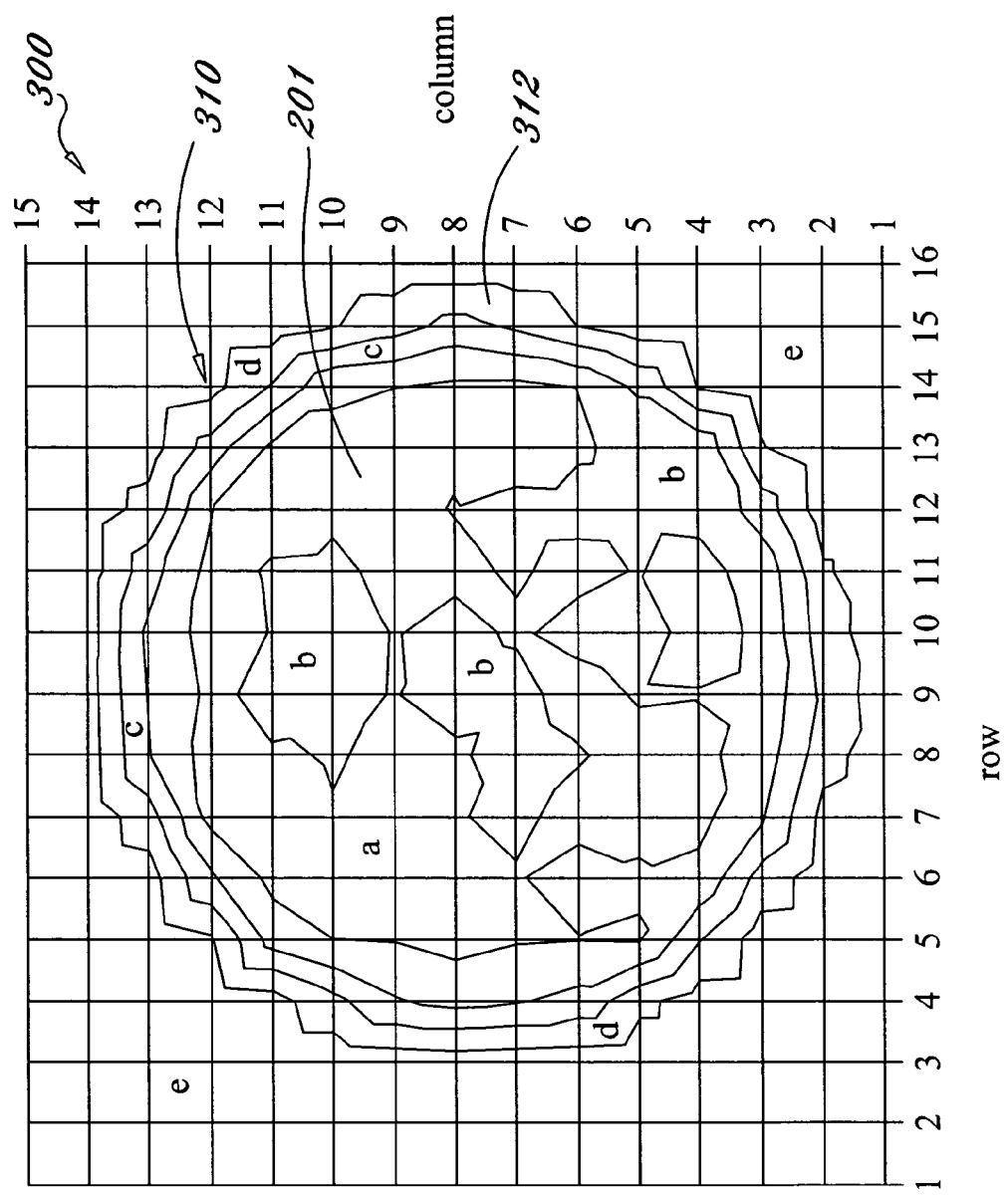
FIG. 5 shows an example of a single region 300 containing output from a single feature.
Figure 5:
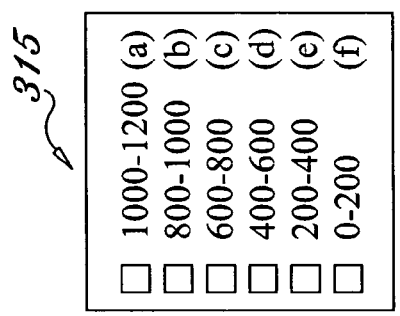

FIG. 5 shows an example of a single region 300 containing a feature 310 from an array. The output shown is for the red channel of a two-channel array. This two dimensional plot shows more clearly the complete coverage of the region by pixels 201 some of which cover the background area of region 300, some of which cover the corona area 312 and some of which cover feature 310 and output higher quality signal than in the corona area. The pixels are tracked by row and column number, and the output values (signals) of the pixels are assembled into a list, which is then sorted according to signal levels. If the array is a two channel array, the signal values are sorted by color and then by signal level (e.g., sort green signals and red signals, and then sort according to signal level within the red group and within the green group). The sort order is ranked by pixel rank number to be used for plotting the signals in their sorted order. FIG. 5 shows a 16×15 grid (i.e., 16 rows of pixels by 15 columns of pixels), which would result in a plotting of 240 pixel signal levels (times two for a two-channel array). This is only an example of a designed grid arrangement, as other sizes and shapes may be employed, as long as the pixel grid areas that capture and separate features are consistent by size and shape according to the design.

A color-coded key for the scanner relative luminance units (RLU) of the pixels shown in FIG. 5 is displayed at 315. which has also been alphabetically coded (i.e., a-e) for purposes of the black and white FIG. 5 of this application. In practice, the plot of FIG. 5 would be color coded. For each color the scanner reads one value for each pixel and the scanner properties define the pixels. Scanner parameters such as offset and calibration settings impact the reported signal. The grid intersections locate the response values in the data spread sheet. The squares are filled-in by interpolation, since contour plots of data (i.e., discrete data points) require interpolation between data points in order to draw the contour plots. Some smoothing is involved. In the example shown, MICROSOFT EXCEL® (spreadsheet software) was used to perform the interpolation. For the data spaced on a grid, Excel aligns coordinate intersections with data points in the plot. Of course, the present invention is not limited to interpolation using MICROSOFT EXCEL®, as other interpolation packages or methodologies may be substituted. The charts are not essential to the invention but merely expose the problem solved by the invention.

Figure 6:
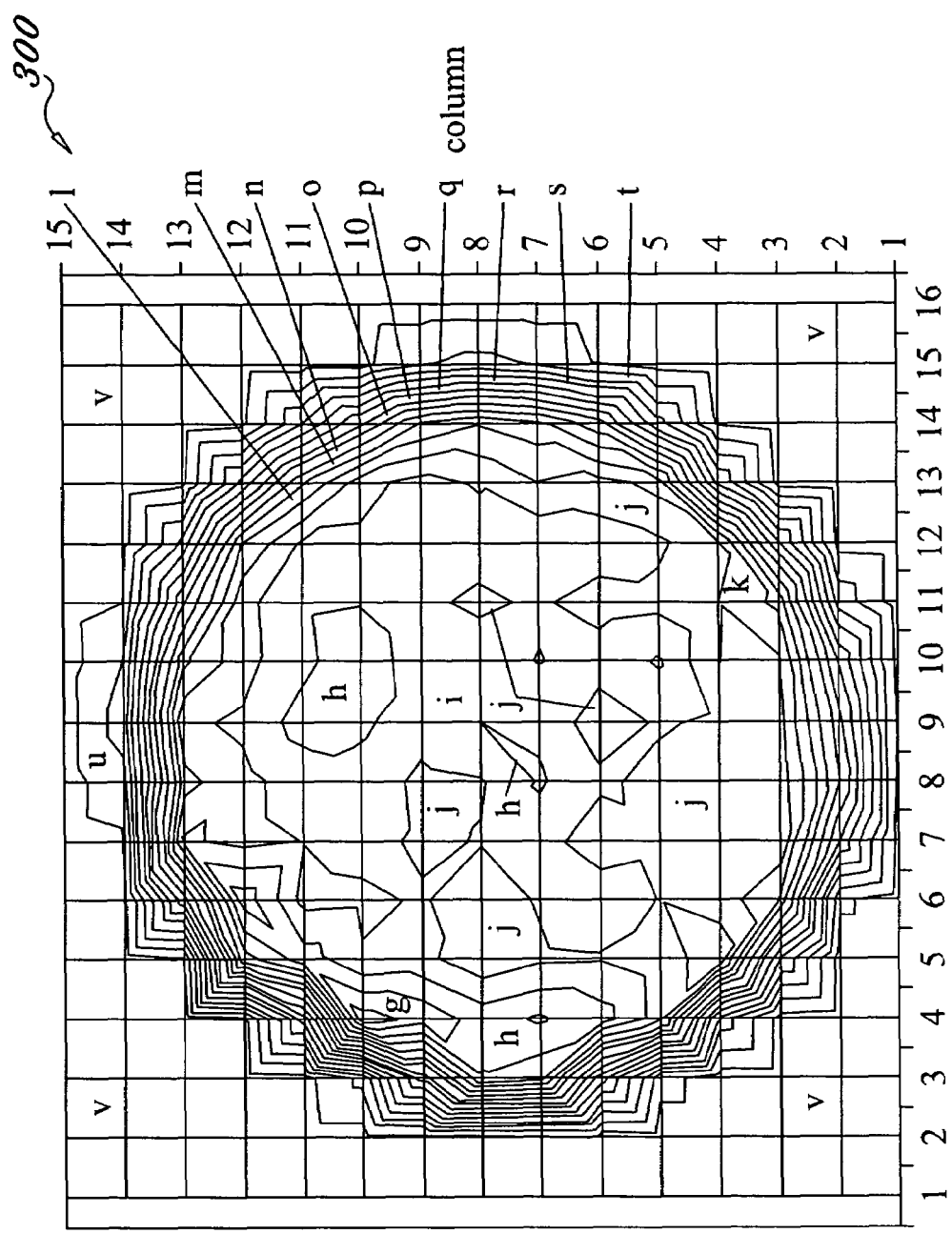
FIG. 6 shows the same grid as shown in FIG. 5, but with both red and green outputs being shown.

FIG. 6 shows the same grid as shown in FIG. 5, but with both red and green outputs being read/overlaid. FIG. 6 shows pixel intensity patterns/contours within a give probe/feature for each (i.e., both) colors. It can be readily observed that the red and green patterns do not match. Since they do not match, comparison of these signals results in noisy differential expression values. Accordingly, the present methods do not calculate differential expression values based upon a one-to-one geographical comparison of signal values.

Figure 7A:
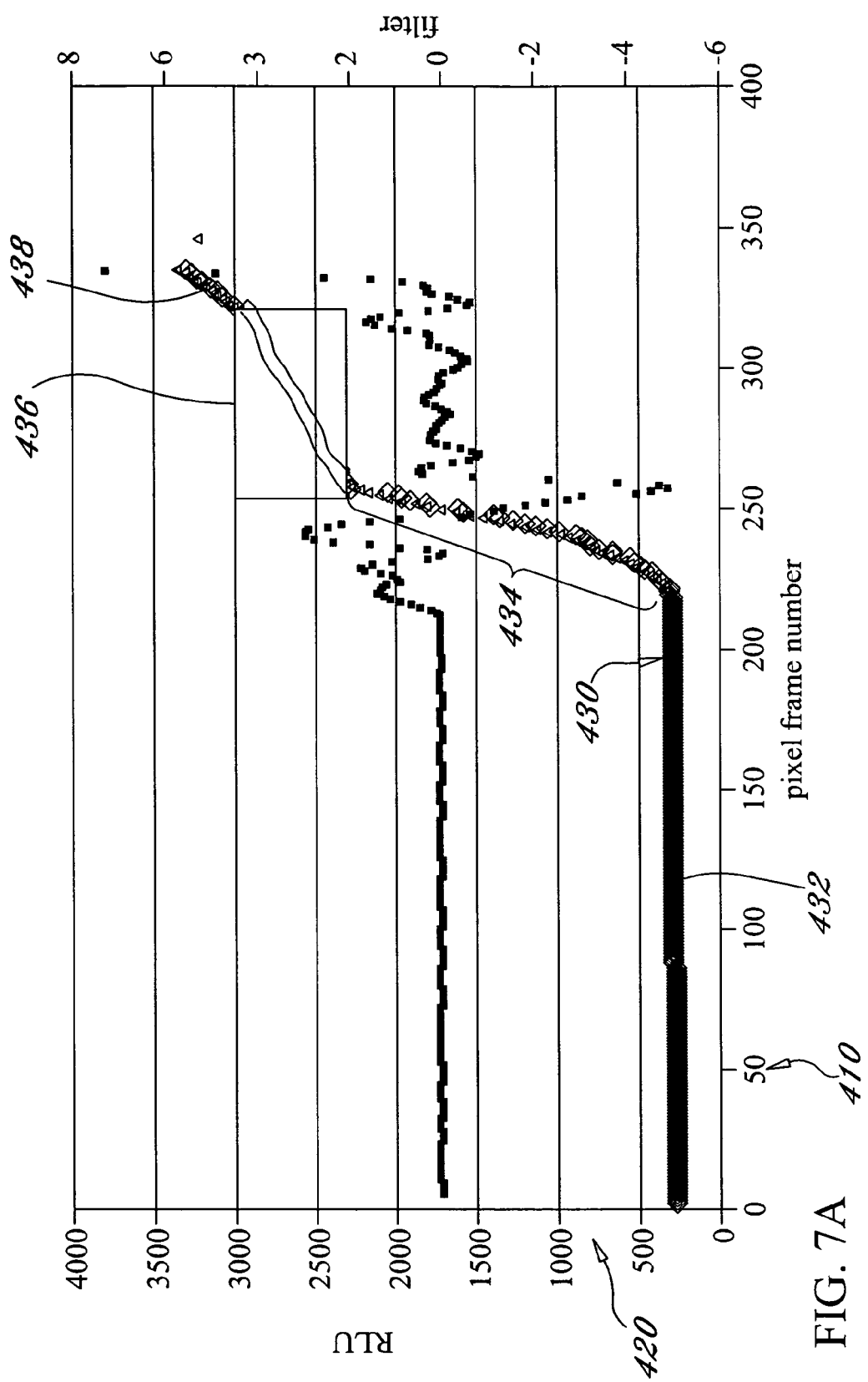
FIG. 7A shows a two-dimensional plot of pixel output values, after sorting.

Rather, after sorting the signal values, the signal values are then plotted on a two-dimensional graph, an example of which is shown in FIG. 7A. The example plotted in FIG. 7A is from a region having 324 pixels (18 rows by 18 columns), also from a two-channel array. The pixel rank number is plotted against the relative luminance units (RLU) to create two-dimensional line plots of the output signals from the region being read. In this example, the green channel is shown by plot 430. The plot 440 is resultant from running a linear filter to identify sections or subsets of the plot 430 that are representative of the highest quality signals, e.g., the "halo section", versus other classes of signals, such as corona section, background section(s) and residue section. As the filter processes the profile 430, it detects curvature in the plot. The filter "turns on" when it detects significant curvature (which may be a predefined expected value assuming a positive signal actually exists), either positive negative, and registers a positive or negative peak, respectively. By further processing these peaks, the filter is able to automatically identify the halo-class section of signals, corona-type section, residue-class section and background section(s) (which may include a "semi-background section). By ranking the signal values and analyzing the resulting profile of ranked signals, this reduces what is a two dimensional problem in the prior art (i.e., finding the best two-dimensional "spot" in a region) to a one-dimensional problem. There are many conventional filters available for analysis of such one-dimensional data, although presently, a Fast Fourier Transform (FFT)-based convolution filter is used for identification of the region containing the highest quality signals, as well as for identification of other sections or subsets of the data. Further information about filters applicable for such use can be found by referring to Haykin, Simon, *Adaptive Filter Theory*, Second Edition, 1991, Prentice Hall, Englewood Cliffs, N.J.; and Press et al., *NUMERICAL RECIPES IN C: The Art of Scientific Computing*, Cambridge University Press, 1988; for example, both of which are incorporated herein, in their entireties, by reference thereto. The relatively low value points which also form a relatively flat slope (i.e., pixel rank numbers 0 to about 210) characterize the background pixels in the region. The highly sloped portion 434 of the plot characterizes the corona region as the output values are transitioning via an increasing portion of active signals from background levels up to the levels of the quality signals. The portion 436 of the plot which has a lesser slope than the corona is the region in which the highest quality signals are found, i.e., the halo class or halo section. The lower the slope of this region, the more consistent and higher quality are the signals produced by the feature. The slope is a result of noise factors present in the manufacture and use of the microarray. The steeper sloped portion 438 at the end of the plot is where spike values, representing residues or portions of the feature that have a relatively high number of errors in the sequences laid down there are found.

Although the pixels have been sorted by signal (intensity) value, the original row and column locations are kept in association with the pixels even when generating the plot shown in FIG. 7A. By studying the coordinate locations associated with the sorted pixels in the plot, patterns in the row/column locations as ordered by the intensity sorting process can be observed, which can be referred to as "banding". Thus, banding of row values may be analyzed, as well as banding of column values. Banding results may then be used for powerful diagnostics, such as estimating a radius (r) of the highest quality pixels by averaging the radii vector magnitudes, relative to the region center, from the row and column locations of the best pixels only. Another example of a diagnostic involves computing individual radii of gyration ($r^2$) for the signal classes designated as the halo or best pixels, coronal pixels, background pixels and residue pixels for diagnostics and comparison. Signal classes are clearly distinguished by the sorted profile and filtering operations, prior to calculation of any coordinate-based diagnostics.

Thus, after sorting the pixels, they are plotted according to the sorting order, and analysis is performed to determine the background, corona (transition area between background and highest signals), best signals, and then residue. Then by applying statistical techniques, such as determining the radius of gyration, for example, as referred to above, the best signal locations in the features are determined. The radius of gyration represents the angular momentum mass. The radius of gyration may optionally be weighted by the signal values of the pixels included in the calculation. Alternatively, a unit of mass may be arbitrarily set to each pixel. As noted, these diagnostics give the radial distribution of the good signals. These are well established diagnostics, the principles of which are further discussed in efunda, "Radius of Gyration Definition", and Peraire, J., "Lecture D11-2D Rigid Body Kinetics: Equations of Motion", Unified Engineering, Spring 2003, Version 1.0, pp 1-8, for example, both of which are incorporated herein, in their entireties, by reference thereto.

Figure 7B:
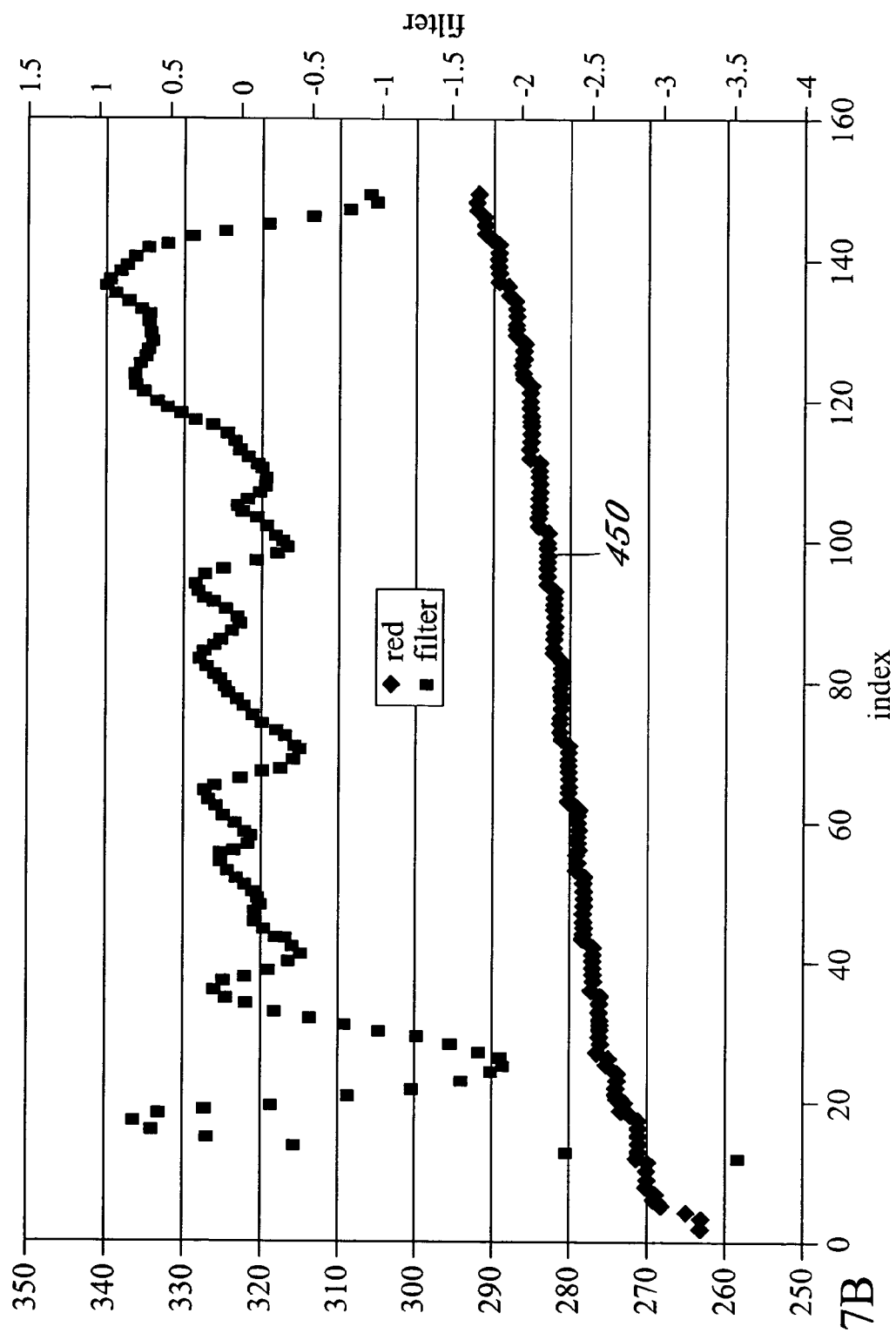
FIG. 7B shows a two-dimensional plot of pixel output values taken from a high density array, from a feature with no detectable signal, after sorting.
Figure 7C:
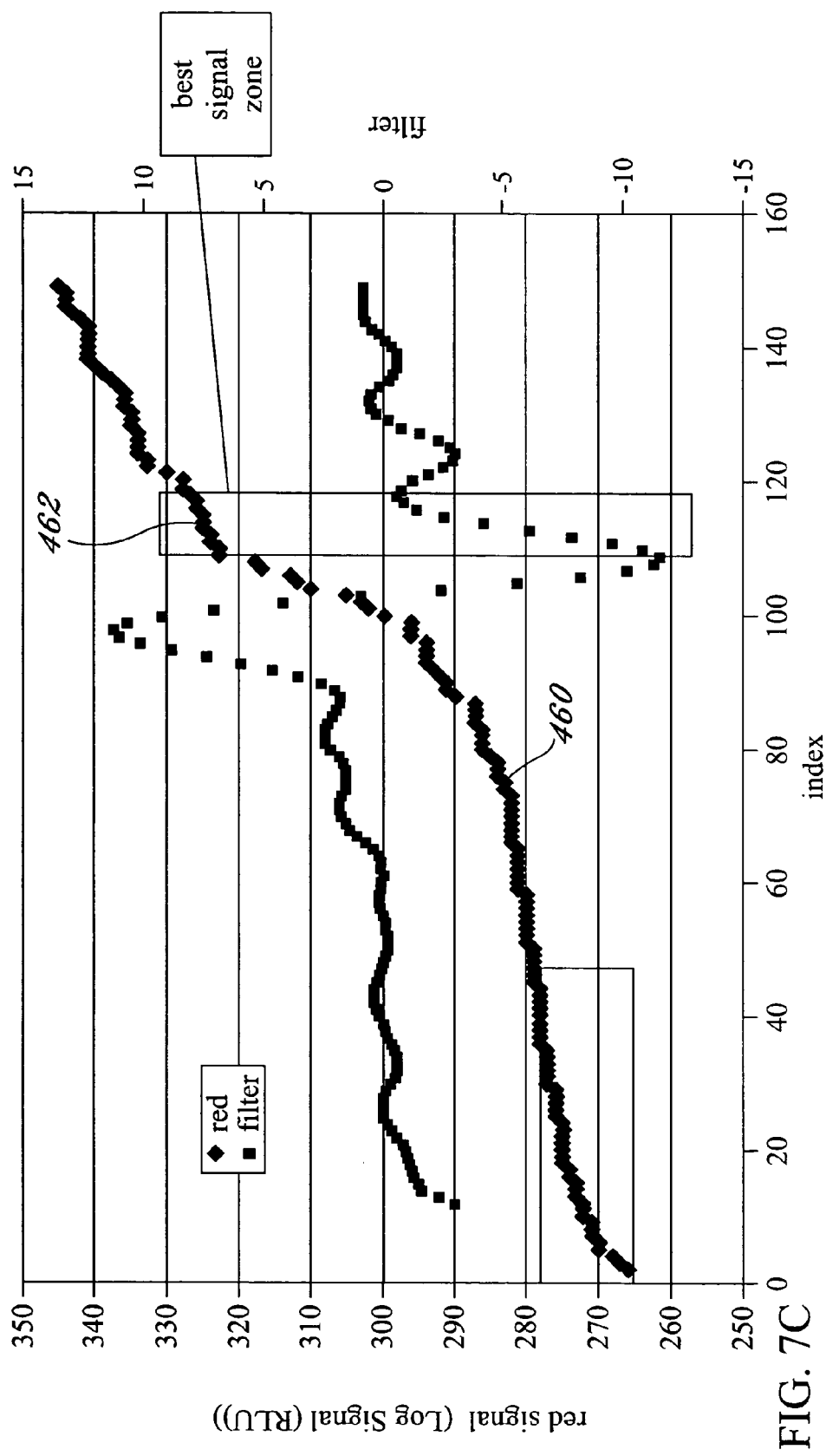
FIG. 7C shows a two-dimensional plot of pixel output values taken from a high density array, from a feature with the weakest detectable signal identified on the array, after sorting.

Shape factors may be developed for each probe. For a specific array design and fixed size and shape (geometry) of features regions, the sorted profile may serve as a shape-template for all features on that platform. Also, coordinate-based diagnostics, as described above, may exhibit standardized properties and thresholds. The one dimensional pixel profile of the sorted intensities exhibits a characteristic shape, as can be observed in FIG. 7A, for example, and this shape can act as a template for signal analysis. For example, by comparing the plots of the sorted intensities for a feature taken from a high density array (hexagonal packed features at a density twice that of the array from which the feature was analyzed in FIG. 7A) which exhibited essentially no signal (i.e., plot 450 in FIG. 7B) with a feature taken from the same array which exhibited the faintest detectable signal (i.e., plot 460 in FIG. 7C), and further comparing both plots 450 and 460 with plot 430, it can readily be observed that even a feature with the faintest signal exhibits a shape factor characteristic of that shown in FIG. 7A and from which a high quality signal section 462 can be identified and used. On the other hand, the "no signal feature" plot 450 does not exhibit the characteristic shape, and no useable section of signals was identified.

By comparing red versus green metrics (or other values from a two-channel array), color-relative alignment metrics may be produced. Color metrics are useful for normalization, e.g., for adjustment of array average intensity levels of each color to correct for noise shifts. Further information about normalization can be found in U.S. Pat. Nos. 6,251, 588 and 6,591,196, both of which are incorporated herein, in their entireties, by reference thereto.

By the present invention, the identification of where one region ends and another begins (e.g., where the corona ends and the "good signal" begins) is relegated to a one-dimensional problem, for which many established utilities are available to solve. Examples of such utilities include linear filters. Prior approaches to signal evaluation, such as the "cookie cutter" methods referred to above, are faced with a two-dimensional problem to solve, which is much more difficult and relies more upon assumptions. By using a linear filter in the present techniques, deep background, semi-background, corona, halo and gummy residues may be identified as partitioned signal classes by filter spikes. The corona captures a mix of background and signaling pixels. The halo pixels are essentially purified with true probe-target signals. As noted above, the filter spikes at major curvature loci in the sorted profile. The spikes, in conjunction with signal levels, mark off the identified sections of the profile.

Ranking of the pixels by intensity or signal strength automatically categorizes the various categories of pixel outputs, as described above. Since the x and y (column and row) locations remain linked to the pixels even after they are ranked, the locations in the feature which outputs the highest quality signals can be easily mapped. As noted above, the best quality signals, indicating the best hybridization results, often tend to occur around the rim or edge of a typical feature.

Once the pixels that give the highest quality signal are determined (e.g., portion 436 in FIG. 7A), statistical evaluations of these pixels may be performed. As noted, the slope of portion 436 indicates the quality or uniformity of the signals outputted by the highest quality regions of the feature. The smaller the standard deviation, as measured by the slope, the higher the quality of the feature. An average (or median, or the like) of the luminance values of the pixels in portion 436 may be calculated for setting the signal level of the feature. By calculating the standard deviation of each pixel within portion 436 from the set value, a measure of the consistency of the signal can be determined.

An estimate of the background signal (e.g., an average of the first 50 to 100 pixel values in a feature region) may optionally be subtracted out from the quantified feature signal, and the same can be done with the other color plot for a two-channel system, to zero balance the signals, such that that background level is considered to be zero. Thus, for example, the same experiment may be done on both red and green channels, and then a ratio may be calculated between the average or otherwise set signal readings of respective features.

Alternatively, pixel by pixel ratios may be computed by comparing red and green pixel output values in the high quality portions of the sorted profiles. Note that this gives a truer differential value, since the pixels are not geographically restricted to the identical location in the feature region, but are compared by their relative ranking in output values. By comparing as to rank, rather than as to geographical positions of the respective pixels for each color, the best signals are used for calculating differential expression levels.

By the above processing, intensity levels for one or two colors may be provided, along with diagnostics for each color, as well as cross-color statistics provided by the comparisons between the two colors (e.g., pixel correlation between the two colors both as sorted and as unsorted (location based)). For example, the median or mean, and standard deviation from the good quality section of the plot for each color may be provided as well as distinction from the background pixels prior to the corona section. These principles apply to many-colored platforms (i.e., platforms having three or more channels) as well.

All pixels that do not fall within the portion that is determined to contain the highest quality signals are ignored for purposes of quantitation. However, these pixels may still be examined for diagnostic purposes, as unusual signals may be indicative of a systematic or processing error that needs to be corrected, for example. Such signals may even provide information about something anomalous that is happening biochemically when running the arrays.

Even for badly distorted features, the present invention is much more adept at retrieving usable signals from such features than currently available methods.

The present techniques have been applied to high quality arrays, as well as to low quality arrays, with acceptable ratios being returned from each category, showing the robustness of the present techniques. Although noise levels for the low quality arrays were greater, they were still within acceptable levels. Further, as noted, the present techniques have been applied to high density arrays and have exhibited superior ability to distinguish faint features (i.e., those features providing very weak signals).

Figure 8:
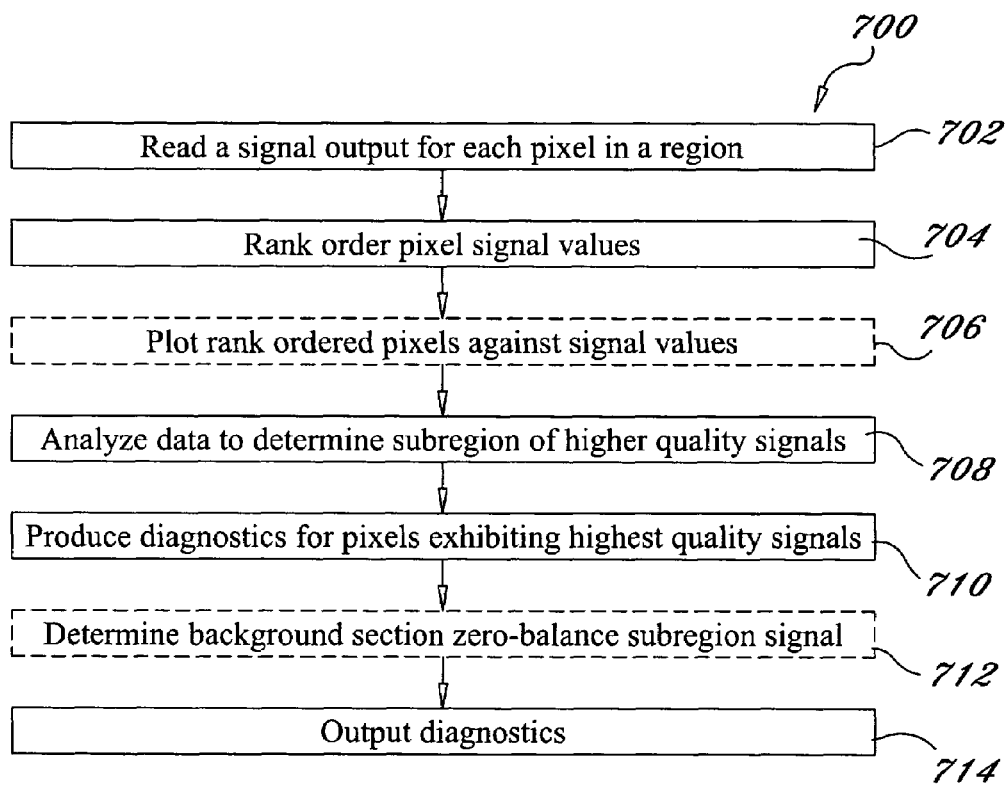
FIG. 8 is a flow chart illustrating processing steps included in the present invention.

Referring to FIG. 8, a flow chart 700 describing processing regions according to the present invention is shown. After locating the grid and determining the locations of each region, a first region is processed to read the signal output of each individual pixel within that region at step 702. At step 704, the pixel signal values are rank ordered in preparation for plotting and processing them. Further information about rank ordering can be found in Press et al., *NUMERICAL RECIPES IN C: The Art of Scientific Computing*, which was incorporated by reference above, and in Johnson et al., *Continuous Univariate Distributions*, Vol. 1, Second Edition, 1994, John Wiley & Sons, which is also incorporated herein, in its entirety, by reference thereto. At step 706, the rank-ordered pixel values are optionally plotted against their relative luminance values in a two-dimensional plot, such as described above with regard to FIG. 7A. It is noted that although such plotting is informative, it is not necessary, since analysis and statistical evaluations may be performed directly from the pixel signal rank list, together with the associated pixel location data. The data (whether from the plot or directly from the rank list) are next analyzed at step 708 to determine the portion or subsection of the profile plot or data list that displays the highest quality signals for the feature being read, such as by filtering, as described above. For example, the beginning of highest quality signal section or halo section may be identified by the first major negative curvature bend in the profile on the high-signal side of the corona section. The halo section then tends to form a substantially linear slope. The slope is a property of the biochemistry of the sequences represented by the signals in the halo section. The flatter the slope, the more consistent are the signals. An upward curvature deviation or spike, from this slope marks the end of the halo section and the beginning of a section containing typically anomalous high signal caused mainly by writer-deformed residue and hybridization wash/dry cycles. Once the subregion of pixels representing the highest quality signals are determined, diagnostics are produced for these pixels at step 710. As noted above, diagnostics that may be performed include determining the radius (r) of the highest quality pixels by averaging the radii vector magnitudes from the row and column locations of the best pixels only, and/or computing a radius of gyration ($r^2$) of the best pixels. Also, means and standard deviation figures for each pixel may be computed relative to these diagnostics. Mean, median or some other average value of pixel signal level may also be computed for the highest quality signals, and standard deviation of each pixel signal value within the subsection may be computed relative to such mean, media or other average. Further reading about such statistical diagnostics can be found in Huber, *Robust Statistics*, 1981, John Wiley & Sons, which is incorporated herein, in its entirety, by reference thereto.

Further optionally, similar diagnostics may be produced for the corona section, residue section and/or background section identified from the rank ordered pixels. The signal range of the subsegment/subsection and/or corona section, residue section and/or background section may also be computed and outputted. Standard errors may also be computed and outputted for and all subsections/sections.

Further optionally, a mean, median or other average signal value representative of the background section may be subtracted from the mean, median or average value (or individually from each pixel value) of the highest signal quality subregion as step 712, to zero-balance" the highest quality signals for comparison with zero-balanced signals from other features. The signals may also be transformed to a log scale by a log transform.

At step 714, the results of processing are outputted, for use by a user interested in obtaining the signal level of the feature having been processed. The main result is a quantified signal with error bars. However, the other diagnostics are useful for array quality scoring and control charts. For example, an output of the ranking of all pixels by sorting may be provided, giving the diagnostic requirement that high rank (i.e., gene abundance) should have a smaller radius relative to low rank signals (e.g., background), by design, within a grid area or zone.

The steps shown in 700 may be repeated for each region containing a feature that a user is interested in reading to obtain a reliable signal from. Additionally, the same processing may be done separately for each channel on any multi-channel platform.

Figure 9:
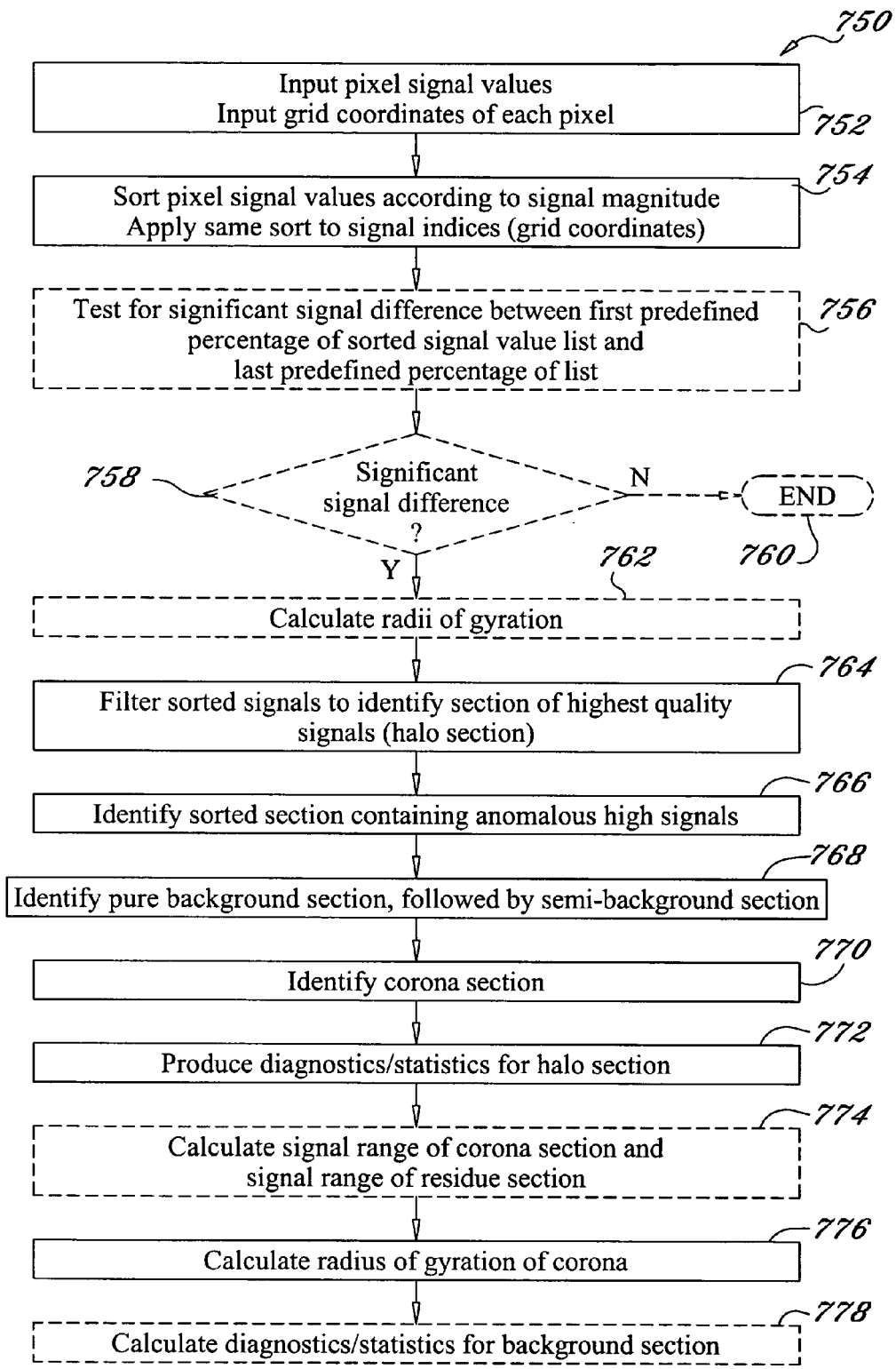
FIG. 9 shows an example of a subroutine 750 for performing diagnostics on a region according to the present invention

FIG. 9 shows an example of a subroutine 750 for performing diagnostics on a region according to the present invention. At step 752, the pixel signal values are inputted. The size of the list (e.g., number of pixels, where higher feature density results in less pixels per feature) may also be inputted, as well as the number of columns and rows in the region being read. The column and row coordinates of each pixel are also inputted to remain associated with each respective pixel having been read.

The pixel signal values are next sorted according to signal value magnitudes, preferably by increasing magnitude, although a sort by decreasing magnitude is possible as well. The same sort is applied to the column and row coordinates associated with the pixels, so that the reordered pixels (resultant from the sort) remain associated with their original coordinates on the grid defining the region.

At step 756, a test may optionally be performed to determined whether a significant signal difference is present between the background of the region and the highest signal levels outputted by the region. A comparison between an average value of a predefined subregion (e.g., the lowest 10% of signal values) at the lowest output signal pixel end of the sorted list is compared with an average value of a predefined subregion (e.g., the highest 10% of signal values) at the highest output signal pixel end of the sorted list. If a significant signal difference is not determined (for example, three time the background noise (as identified using error bars) from the background section of the sorted profile, although other predefined multipliers may be used), then there is too much error in the region to take reliable signal readings from. For example, the feature in the region may be inactive (e.g., "black hole") or there may be too much noise in the background to separate the background from the feature. With such a finding, processing ends with regard to this region, thereby saving processing time which would be wasted on a region that will not provide reliable signal readings.

If a significant difference is found, then radii of gyration may be calculated for the lowest rank predefined subsegment and highest rank predefined subsegment at step 762. The radius of gyration of the highest predefined subregion should have a smaller radius of gyration than that of the lowest predefined subregion (e.g., the ratio is typically about 7 to 8) unless the feature is severely off center in the region or is inactive (e.g., black hole). If this is not the case, then it is possible that the region has not completely captured the feature, due to grid misalignment or drift, for example, and the process should be halted and marked as a failure at this point, after which the grid zone may be adjusted to redefine regions so that each region completely captures a feature. Readjustment of the grid zone may be performed according to any of the techniques described above, while varying one or more parameters, such as the starting point or points for a DynaCluster procedure, for example, or by changing a window size in the projection technique. Other approaches may be made also by modifying one or more parameters in the process used to redefine the grid zone.

At step 764 a section or subregion of the sorted signals are identified, through use of a linear filter, as representing the highest quality signals in the region. These are sometimes also referred to as "halo signals".

Once the section containing the highest quality signals has been identified, it is a simple matter to identify the sorted section containing anomalous high level signals (e.g., caused by writer/depurination residues, etc.) at step 766, as this is simply all of the sorted pixel signal values which are greater than the greatest value in the section containing the highest quality signals.

At step 768, a section of the sorted signals which are representative of the background (e.g., "deep" or "pure" background) is identified, followed by a semi-background section that is between the pure background section and corona section. The remaining section that has values less than the halo signals section, but greater than the values in the background and semi-background sections, is identified as the corona section at step 770.

Diagnostics/statistics are produced and outputted to characterize the halo section at step 772. Examples of metrics that may be produced to characterize the optimal signal as found in the halo section include signal range, mean/median/average signal value, radius of gyration, standard deviation as to average signal value and/or average radius of gyration.

Optionally, the signal ranges of the corona section and residue section may be calculated and outputted at step 774. Further optionally, calculation and output of the two corona sections may be made to track the scanner direction on each halo edge of the feature as it scans. These boundaries may be used as a comparison basis between two colors for a two channel array on a feature, to check scanner color alignment, since the ratio differential between the upper and lower corona sections is especially sensitive to scanner color alignment, since the corona region is that region where the rate of change of signal values from pixel to pixel is highest. However, as already noted, misalignment of channels does not effect the results of the present invention, since comparisons of signal values are based upon rank order and therefore are not effected by the locations of the pixels from which the signals originated.

At step 776, a radius of gyration of the corona section is calculated and outputted. This is a useful measure of the feature spot size.

Further optionally, diagnostics/statistics for the background sections may be calculated and outputted at step 778. Metrics that may be calculated and outputted include, but are not limited to signal range, means and standard deviation.

Figure 10:
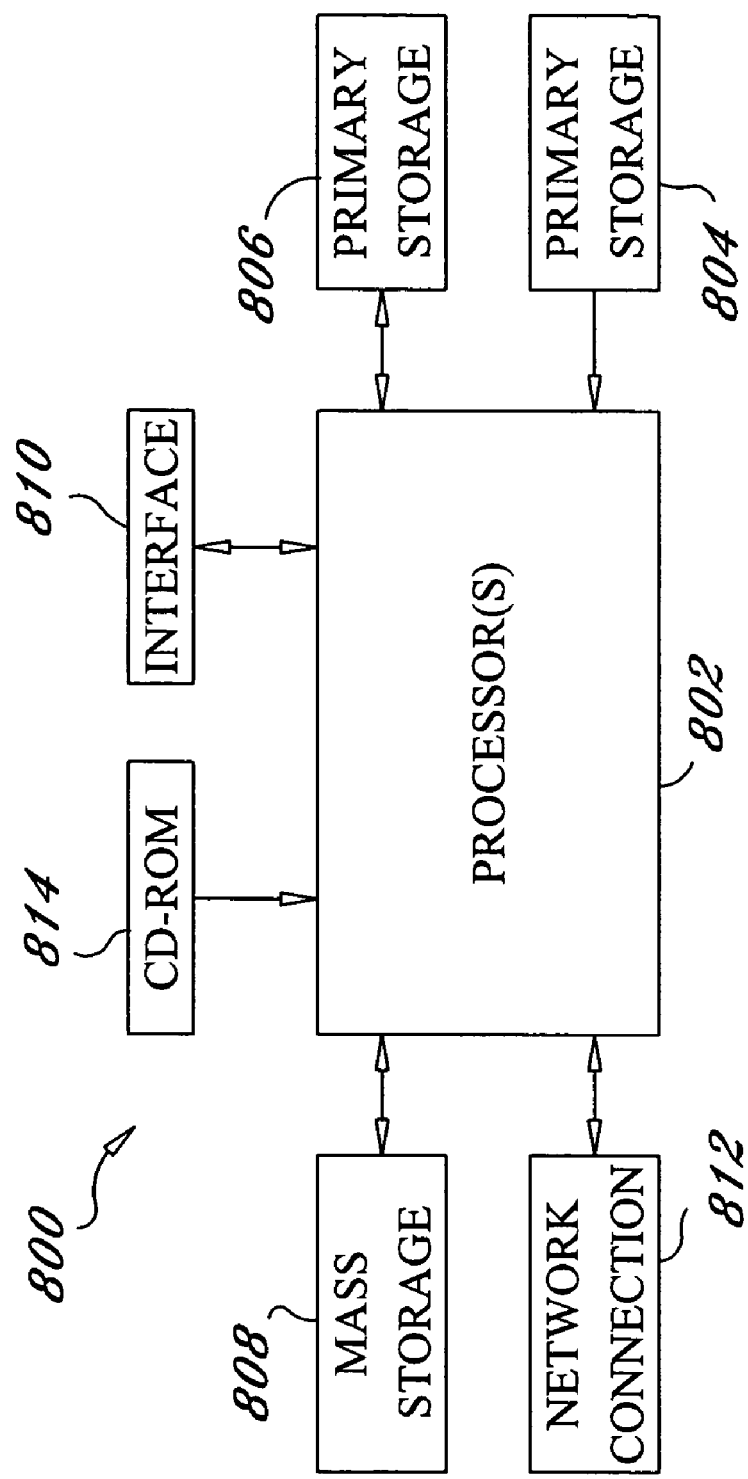
FIG. 10 illustrates a typical computer system that may be employed in accordance with the present invention.

FIG. 10 illustrates a typical computer system in accordance with an embodiment of the present invention. The computer system 800 includes any number of processors 802 (also referred to as central processing units, or CPUs) that are coupled to storage devices including primary storage 806 (typically a random access memory, or RAM), primary storage 804 (typically a read only memory, or ROM). As is well known in the art, primary storage 804 acts to transfer data and instructions uni-directionally to the CPU and primary storage 806 is used typically to transfer data and instructions in a bi-directional manner Both of these primary storage devices may include any suitable computer-readable media such as those described above. A mass storage device 808 is also coupled bi-directionally to CPU 802 and provides additional data storage capacity and may include any of the computer-readable media described above. Mass storage device 808 may be used to store programs, data and the like and is typically a secondary storage medium such as a hard disk that is slower than primary storage. It will be appreciated that the information retained within the mass storage device 808, may, in appropriate cases, be incorporated in standard fashion as part of primary storage 806 as virtual memory. A specific mass storage device such as a CD-ROM 814 may also pass data uni-directionally to the CPU.

CPU 802 is also coupled to an interface 810 that includes one or more input/output devices such as such as video monitors, track balls, mice, keyboards, microphones, touch-sensitive displays, transducer card readers, magnetic or paper tape readers, tablets, styluses, voice or handwriting recognizers, or other well-known input devices such as, of course, other computers. Finally, CPU 802 optionally may be coupled to a computer or telecommunications network using a network connection as shown generally at 812. With such a network connection, it is contemplated that the CPU might receive information from the network, or might output information to the network in the course of performing the above-described method steps. The above-described devices and materials will be familiar to those of skill in the computer hardware and software arts.

The hardware elements described above may implement the instructions of multiple software modules for performing the operations of this invention. For example, instructions for plotting ranked pixel values may be stored on mass storage device 808 or 814 and executed on CPU 808 in conjunction with primary memory 806.

In addition, embodiments of the present invention further relate to computer readable media or computer program products that include program instructions and/or data (including data structures) for performing various computer-implemented operations. The media and program instructions may be those specially designed and constructed for the purposes of the present invention, or they may be of the kind well known and available to those having skill in the computer software arts. Examples of computer-readable media include, but are not limited to, magnetic media such as hard disks, floppy disks, and magnetic tape; optical media such as CD-ROM, CDRW, DVD-ROM, or DVD-RW disks; magneto-optical media such as floptical disks; and hardware devices that are specially configured to store and perform program instructions, such as read-only memory devices (ROM) and random access memory (RAM). Examples of program instructions include both machine code, such as produced by a compiler, and files containing higher level code that may be executed by the computer using an interpreter.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

That which is claimed is:

1. A method for obtaining quality output signals from a chemical array image, said method comprising the steps of:
   rank ordering the output signals from the chemical array image according to signal magnitude;
   plotting the output signal magnitudes versus rank order numbers on a two-dimensional plot;
   determining a slope of the plotted subset of the rank ordered output signals which are representative of the quality signals, thereby identifying a subset of the rank ordered output signals which are representative of the quality signals; and
   determining a relative quality of the subset of quality signals based on said slope.

2. A method for obtaining quality output signals from a chemical array image, said method comprising the steps of:
   rank ordering the output signals from the chemical array image according to signal magnitude, wherein the chemical array image is broken down in to subunits, and coordinates of a location of each subunit of the chemical array image are maintained with the signal values even after said rank ordering;
   identifying a subset of the rank ordered output signals which are representative of the quality signals;
   identifying banding of subunits by comparing the rank order of the subunit signal outputs with said coordinates of the subunits; and
   producing diagnostics based on results of said identifying banding, wherein said producing diagnostics includes at least one of estimating a radius of at least one of said subsets, and computing a radius of gyration of at least one of said subsets.

3. A method for obtaining quality output signals from a chemical array image, said method comprising the steps of:
   rank ordering the output signals from the chemical array image according to signal magnitude, wherein the chemical array image is broken down into subunits, and coordinates of a location of each subunit of the chemical array image are maintained with the signal values even after said rank ordering; and
   identifying a subset of the rank ordered output signals which are representative of the quality signals;
   wherein said steps are carried out for two channels or colors of subunits, said method further comprising comparing the output signals of the first channel to the second channel to check for misalignment of the channels.

4. A method for obtaining quality output signals from a chemical array image, said method comprising the steps of: and
   identifying a subset of the rank ordered output signals which are representative of the quality signals, wherein said steps are carried out for two channels or colors of signals, said method further comprising comparing signals between the two channels according to rank order, not physical location on the chemical array image.

5. A method for obtaining quality output signals from a chemical array image, said method comprising the steps of:
   rank ordering the output signals from the chemical array image according to signal magnitude;
   identifying a subset of the rank ordered output signals which are representative of the quality signals;
   identifying a background subset comprising a subset of the rank ordered output signals having the lowest magnitudes; and identifying a corona subset comprising a subset of the rank ordered output signals having transitional magnitude values between the values of said background subset and said subset having the high quality signals; and identifying two corona section locations to be used for comparison with two corona sections identified in a second channel of a two channel array, to check color alignment.

6. A system for obtaining quality signals from a chemical array image, said system comprising:

means for rank ordering the output signals from reading the chemical array image, according to signal magnitude;

means for identifying a subset of the rank ordered output signals which are representative of the quality signals;

means for identifying a background subset comprising a subset of the rank ordered output signals having the lowest magnitudes;

means for identifying a corona subset comprising a subset of the rank ordered output signals having transitional magnitude values between the values of said background subset and said subset having the quality signals; and means for identifying two corona section locations to be used for comparison with two corona sections identified in a second channel of a two channel array, to check color alignment.

7. The method of claim 1, wherein the region is subdivided into pixels, and each ranked output signal is a signal representing output from a pixel.

8. The method of claim 1, wherein said identifying a subset is performed using a filter.

9. The method of claim 1, wherein coordinates of a location of each region of the chemical array image are maintained with the signal values even after said rank ordering.

10. The method of claim 1, further comprising identifying a residue subset comprising a subset of the rank ordered output signals having magnitudes larger than the quality output signals subset.

11. The method of claim 1, further comprising identifying a background subset comprising a subset of the rank ordered output signals having the lowest magnitudes.

12. The method of claim 11, further comprising identifying a corona subset comprising a subset of the rank ordered output signals having transitional magnitude values between the values of said background subset and said subset having the quality output signals.

13. The method of claim 9, further comprising identifying banding of subunits by comparing the rank order of the subunit signal outputs with said coordinates of the subunits.

14. The method of claim 13, further comprising producing diagnostics based on results of said identifying banding.

15. The method of claim 14, wherein said producing diagnostics includes at least one of calculating a mean, median or other estimate of signal values in at least one of said subsets, and calculating a standard deviation of signal values in at least one of said subsets.

16. The method of claim 11, further comprising subtracting an average signal value of said background subset from an average value of said subset having the quality output signals.

17. A method comprising forwarding a result obtained from the method of claim 1 to a remote location.

18. A method comprising transmitting data representing a result obtained from the method of claim 1 to a remote location.

19. A method comprising receiving a result obtained from a method of claim 1 from a remote location.

20. The method of claim 1, wherein the chemical array image is taken from a microarray.

21. The method of claim 1, further comprising the steps of:

comparing an average signal value from a first predefined subset made up of the lowest signal values in the rank ordering with an average signal value from a second predefined subset made up of the high signal values in the rank ordering to determine whether a predefined signal difference level is present.

22. The method of claim 1, further comprising iterating said reading and rank ordering steps for at least one additional region.

23. The method of claim 1, further comprising locating a grid to define said regions.

24. The method of claim 23, wherein said locating comprises providing at least one mathematical probe to converge on the features of the array, calculating a distance between features having been converged on, and calculating a size of said regions said size being sufficient to completely contain a single feature.

* * * * *